(12) United States Patent
Menzel et al.

(10) Patent No.: US 12,239,792 B2
(45) Date of Patent: Mar. 4, 2025

(54) METHOD AND DEVICE FOR CONTROLLING THE TEMPERATURE OF THE GAS FLOW IN MEDICAL DEVICES

(71) Applicant: W.O.M. World of Medicine GmbH, Berlin (DE)

(72) Inventors: Felix Menzel, Berlin (DE); Andreas Zeyssig, Berlin (DE); Johannes Korner, Weingarten (DE)

(73) Assignee: W.O.M. World of Medicine GmbH, Berlin (DE)

( * ) Notice: Subject to any disclaimer, the term of this patent is extended or adjusted under 35 U.S.C. 154(b) by 983 days.

(21) Appl. No.: 17/240,589

(22) Filed: Apr. 26, 2021

(65) Prior Publication Data

US 2021/0346636 A1    Nov. 11, 2021

Related U.S. Application Data

(63) Continuation of application No. 15/547,291, filed as application No. PCT/DE2016/000027 on Jan. 27, 2016, now Pat. No. 12,023,446.

(30) Foreign Application Priority Data

Jan. 27, 2015   (DE) .......................... 102015000845.5

(51) Int. Cl.
*A61M 16/10*   (2006.01)
*A61M 13/00*   (2006.01)
(Continued)

(52) U.S. Cl.
CPC ........ *A61M 16/1095* (2014.02); *A61M 13/00* (2013.01); *A61M 13/003* (2013.01);
(Continued)

(58) Field of Classification Search
CPC .......... A61B 18/14; A61B 2017/00482; A61B 2018/00166; A61B 2018/00178;
(Continued)

(56) References Cited

U.S. PATENT DOCUMENTS 3,789,190 A   1/1974   Orosy
3,954,920 A   5/1976   Heath
(Continued)

FOREIGN PATENT DOCUMENTS

DE        19545719 A1    6/1997
DE       102015000845    7/2016

OTHER PUBLICATIONS

Isermann R (2008). Mechatronische Systeme. Grundlagen. Springer-Verlag: Berlin.
(Continued)

*Primary Examiner* — Annette Dixon
(74) *Attorney, Agent, or Firm* — McCarter & English, LLP

(57) ABSTRACT

Disclosed are methods for measuring and controlling the gas temperature in medical procedures. In embodiments of the disclosed methods a gas is supplied to a patient using a gas supply device and a supply line. A heating system heats the gas using a heating wire prior to the gas being provided to the patient. A controller electrically controls the heating power of the heating wire based on an estimated value of a temperature at an exit of the heating system obtained from a mathematical estimation system, wherein a resistance of the heating wire is an input variable of the mathematical estimation system.

13 Claims, 9 Drawing Sheets

(51) Int. Cl.
*A61M 16/08* (2006.01)
*G05D 23/19* (2006.01)

(52) U.S. Cl.
CPC ..... *A61M 16/0875* (2013.01); *G05D 23/1917* (2013.01); *A61M 2202/0208* (2013.01); *A61M 2202/0225* (2013.01); *A61M 2205/3368* (2013.01); *A61M 2205/3653* (2013.01); *A61M 2205/50* (2013.01)

(58) Field of Classification Search
CPC   A61B 2018/00666; A61B 2018/00678; A61B 2018/00708; A61B 2018/00791; A61B 2018/00797; A61B 2018/00815; A61B 2018/00821; A61B 2018/00988; A61B 2562/08; A61B 5/028; A61B 5/1495; A61B 5/6855; A61B 5/6856; A61B 5/6857; A61M 13/003; A61M 16/0012; A61M 16/0051; A61M 16/0066; A61M 16/0069; A61M 16/024; A61M 16/026; A61M 16/0465; A61M 16/0666; A61M 16/0841; A61M 16/0875; A61M 16/1075; A61M 16/1085; A61M 16/109; A61M 16/1095; A61M 16/16; A61M 16/161; A61M 2016/0039; A61M 2205/3368; A61M 2205/3372; A61M 2205/3653; A61M 2205/7518; A61M 2205/7536; A61M 2205/7545; A61M 2205/8206; G05D 23/2401; G06F 30/20; H01M 10/482; H01M 10/486; H01M 10/613; H01M 10/633; H02P 21/141; Y02E 60/10
See application file for complete search history.

(56) References Cited

U.S. PATENT DOCUMENTS

| | | | |
|---|---|---|---|
| 4,621,632 A * | 11/1986 | Bartels | A61M 16/16 |
| | | | 261/130 |
| 5,246,419 A | 9/1993 | Absten | |
| 5,411,474 A * | 5/1995 | Ott | A61M 16/16 |
| | | | 604/23 |
| 5,476,447 A | 12/1995 | Noda et al. | |
| 5,553,622 A | 9/1996 | McKown et al. | |
| 5,558,084 A | 9/1996 | Daniell et al. | |
| 5,588,423 A | 12/1996 | Smith | |
| 6,010,118 A | 1/2000 | Milewicz | |
| 6,068,609 A | 5/2000 | Ott et al. | |
| 6,299,147 B1 | 10/2001 | Mitter | |
| 6,349,722 B1 | 2/2002 | Gradon et al. | |
| 6,584,972 B2 | 7/2003 | McPhee | |
| 6,598,604 B1 | 7/2003 | Seakins | |
| 6,745,766 B2 | 6/2004 | Fini | |
| 6,827,340 B2 | 12/2004 | Austin et al. | |
| 6,842,314 B2 | 1/2005 | Sasaki et al. | |
| 6,968,841 B2 | 11/2005 | Fini | |
| 6,976,489 B2 | 12/2005 | Mantell et al. | |
| 7,040,315 B1 | 5/2006 | Stromberg | |
| 7,066,902 B1 | 6/2006 | Ott et al. | |
| 7,204,248 B2 | 4/2007 | Enk | |
| 7,250,035 B1 | 7/2007 | Ott et al. | |
| 7,322,566 B2 | 1/2008 | Anthony | |
| 7,425,210 B2 | 1/2008 | Anthony | |
| 7,449,007 B2 | 11/2008 | Ott et al. | |
| 7,455,653 B2 | 11/2008 | Ott et al. | |
| 7,476,212 B2 | 1/2009 | Spearman et al. | |
| 7,647,925 B2 | 1/2010 | Mantell et al. | |
| 7,731,704 B2 | 6/2010 | Ott et al. | |
| 7,744,557 B2 | 6/2010 | Ott et al. | |
| 7,762,251 B2 | 7/2010 | Mantell et al. | |
| 7,811,253 B2 | 10/2010 | Hart et al. | |
| 7,918,816 B2 | 4/2011 | Ott et al. | |
| 7,975,687 B2 | 7/2011 | Grundler et al. | |
| 7,997,270 B2 | 8/2011 | Meier | |
| 8,091,546 B2 | 1/2012 | Mantell et al. | |
| 8,118,769 B2 | 2/2012 | Diemunsch | |
| 8,133,196 B2 | 3/2012 | Hart et al. | |
| 8,147,442 B2 | 4/2012 | Ott et al. | |
| 8,181,940 B2 | 5/2012 | Payne et al. | |
| 8,206,337 B2 | 6/2012 | Blackhurst et al. | |
| 8,211,052 B1 | 7/2012 | Ott et al. | |
| 8,240,306 B2 | 8/2012 | Cortez, Jr. et al. | |
| 8,269,638 B2 | 9/2012 | Lloyd et al. | |
| 8,333,195 B2 | 12/2012 | Cortez, Jr. et al. | |
| 8,356,593 B2 | 1/2013 | Cortez, Jr. et al. | |
| 8,444,591 B2 | 5/2013 | Temple | |
| 8,544,461 B2 | 10/2013 | Grundler et al. | |
| 12,023,446 B2 * | 7/2024 | Menzel | G05D 23/1917 |
| 2002/0000783 A1 | 1/2002 | Maceratini et al. | |
| 2002/0072700 A1 | 6/2002 | Mantell et al. | |
| 2002/0112725 A1 * | 8/2002 | Thudor | A61M 16/1085 |
| | | | 128/203.16 |
| 2002/0139367 A1 | 10/2002 | McPhee | |
| 2004/0154617 A1 | 8/2004 | Dietmar | |
| 2005/0107766 A1 | 5/2005 | Ott et al. | |
| 2005/0107767 A1 | 5/2005 | Ott et al. | |
| 2005/0113795 A1 | 5/2005 | Ott et al. | |
| 2005/0113797 A1 | 5/2005 | Ott et al. | |
| 2006/0033223 A1 | 2/2006 | Mantell et al. | |
| 2006/0052742 A1 | 3/2006 | Ott et al. | |
| 2006/0129098 A1 | 6/2006 | Hart et al. | |
| 2006/0151624 A1 | 7/2006 | Grundler et al. | |
| 2006/0184096 A1 | 8/2006 | Ott et al. | |
| 2007/0107726 A1 | 5/2007 | Mantell et al. | |
| 2010/0163044 A1 | 7/2010 | Mantell et al. | |
| 2010/0241061 A1 | 9/2010 | Ott et al. | |
| 2010/0312416 A1 | 12/2010 | Demirdelen | |
| 2011/0028890 A1 | 2/2011 | Hart et al. | |
| 2011/0106001 A1 | 5/2011 | Ott et al. | |
| 2011/0166506 A1 | 7/2011 | Ott et al. | |
| 2011/0230820 A1 | 9/2011 | Lillis et al. | |
| 2011/0288474 A1 | 11/2011 | Ott et al. | |
| 2011/0306925 A1 | 12/2011 | Mantell et al. | |
| 2012/0074601 A1 | 3/2012 | Payne et al. | |
| 2012/0172790 A1 | 7/2012 | Hart et al. | |
| 2012/0238947 A1 | 9/2012 | Ott et al. | |
| 2013/0073013 A1 | 3/2013 | Pujol | |
| 2013/0249697 A1 | 9/2013 | Lloyd et al. | |
| 2014/0050951 A1 * | 2/2014 | Fleckenstein | H01M 10/486 |
| | | | 703/2 |
| 2014/0166005 A1 * | 6/2014 | Tatkov | A61M 16/0465 |
| | | | 128/203.14 |

OTHER PUBLICATIONS

Felix Menzel: "Beobachtergestlitzte Regelung einer Gasheizung in der Minimal-Invasiven-Medizin (kurz MIM)", May 12, 2015 (May 12, 2015), pp. 1-21, XP055270174, http://spectronet.de/story_docs/vortraege_2015/150512_matlab_expo2015/150512_18_menzel_wom.pdf.
PCT International Search Report and Written Opinion dated May 17, 2016 for PCT Application No. PCT/DE2016/000027.
PCT/DE2016/000027, Jan. 27, 2016, WO/2016/119773.
U.S. Appl. No. 15/547,291, filed Feb. 15, 2016, US 2018-0147384 A1.

* cited by examiner

Equation 1

$dQ_3 = \alpha(\vartheta - \sigma) \cdot dA \cdot dt$

Equation 2

$dQ_{Dr} = \rho_{Dr} \cdot dV_{Dr} \cdot c_{Dr} \cdot \dfrac{\partial \sigma}{\partial t} dt$ $\Leftrightarrow dQ_{Dr} = \rho_{Dr} \cdot dA_{Dr} \cdot dx \cdot c_{Dr} \cdot \dfrac{\partial \sigma}{\partial t} dt$ Equation 3

$dQ_{el} = \dfrac{P_{el} \cdot dt \cdot dx}{l_{HZ}}$

Equation 4

$dQ_{Dr} = dQ_3 + dQ_{el}$

Equation 5

$\dot{\sigma} = -\dfrac{\alpha \cdot \pi \cdot d_{Dr}}{\rho_{Dr} \cdot A_{Dr} \cdot c_{Dr}} \cdot \sigma + \dfrac{\alpha \cdot \pi \cdot d_{Dr}}{\rho_{Dr} \cdot A_{Dr} \cdot c_{Dr}} \cdot \vartheta + \dfrac{1}{2 \cdot \rho_{Dr} \cdot A_{Dr} \cdot c_{Dr} \cdot l_{HZ}} \cdot P_{el}$ Equation 6 (comparison)

$\dot{x} = -A \cdot x + B \cdot u + E \cdot d$

FIG. 3

$$\begin{bmatrix} \dot{\vartheta} \\ \dot{\sigma} \\ \dot{\eta} \end{bmatrix} = \begin{bmatrix} \dfrac{-\left(\pi \cdot (2 \cdot \alpha \cdot d_{Dr} + \beta \cdot d_{Si}) + \dfrac{\dot{V}}{A_{Str} \cdot l_{Hz}}\right)}{\rho_F \cdot A_{Str} \cdot c_F} & \dfrac{2 \cdot \alpha \cdot \pi \cdot d_{Dr}}{\rho_F \cdot A_{Str} \cdot c_F} & \dfrac{\beta \cdot \pi \cdot d_{Si}}{\rho_F \cdot A_{Str} \cdot c_F} \\ \dfrac{\alpha \cdot \pi \cdot d_{Dr}}{\rho_{Dr} \cdot A_{Dr} \cdot c_{Dr}} & \dfrac{\alpha \cdot \pi \cdot d_{Dr}}{\rho_{Dr} \cdot A_{Dr} \cdot c_{Dr}} & 0 \\ \dfrac{\beta \cdot \pi \cdot d_{Si}}{\rho_S \cdot A_S \cdot c_S} & 0 & \dfrac{-\pi \cdot (\beta \cdot d_{Si} + \gamma \cdot d_{Sa})}{\rho_S \cdot A_S \cdot c_S} \end{bmatrix} \cdot \begin{bmatrix} \vartheta \\ \sigma \\ \eta \end{bmatrix}$$

$$+ \begin{bmatrix} 0 & 0 & 0 \\ 0 & \dfrac{1}{2 \cdot \rho_{Dr} \cdot A_{Dr} \cdot c_{Dr} \cdot l_{Hz}} & 0 \\ 0 & 0 & 0 \end{bmatrix} \cdot \begin{bmatrix} 0 \\ P_{el} \\ 0 \end{bmatrix}$$

$$+ \begin{bmatrix} \dfrac{\dot{V}}{A_{Str} \cdot l_{Hz}} & 0 & 0 \\ 0 & 0 & 0 \\ 0 & 0 & \dfrac{\gamma \cdot \pi \cdot d_{Sa}}{\rho_S \cdot A_S \cdot c_S} \end{bmatrix} \cdot \begin{bmatrix} \vartheta_E \\ 0 \\ \xi \end{bmatrix}$$

FIG. 4

METHOD AND DEVICE FOR CONTROLLING THE TEMPERATURE OF THE GAS FLOW IN MEDICAL DEVICES

CROSS-REFERENCE TO REFLATED APPLICATIONS

This application is a continuation of U.S. patent application Ser. No. 15/547,291, filed on Jul. 28, 2017, entitled METHOD AND DEVICE FOR CONTROLLING THE TEMPERATURE OF THE GAS FLOW IN MEDICAL DEVICES, which is a national stage application based on PCT International Application No. PCT/DE2016/000027, filed on Jan. 27, 2016, claiming the benefit of priority to German Patent Application No. DE 10 2015 000845.5, the entire contents of each of these applications are hereby incorporated by reference.

FIELD

The present invention relates to a method for controlling the gas temperature in medical devices, e.g. in the field of laparoscopy or respiration, and to devices for carrying-out said method.

BACKGROUND OF THE INVENTION

In various medical procedures, gases are introduced into the inward parts of the body. An example thereof is the laparoscopy, wherein up to now during a therapeutic intervention gases (e.g., $CO_2$) are supplied to the abdomen. In these procedures the supplied gas is normally heated, so that the gas entering into the inward parts of the body has nearly body temperature, since too cold as well as too hot gases would lead to pain symptoms of the patient. Therefore, measurement and control of the gas temperature are particularly important. Typically, the gas lines used for such procedures are provided with temperature sensors that are intended to allow a corresponding temperature control. The use of such separate sensors is disadvantageous, among other reasons, since they cause additional cost. Since the associated hoses are disposable articles, it is desirable to avoid any additional cost. Another possibility of measuring the temperature is the measurement of the temperature of the heating wire. There is a relationship between the gas temperature at the exit of the hose and the temperature of the heating wire, it is however dependent on a number of parameters, such as, e.g., the volume flow of the gas, the type of gas, the heating power, the geometry, and the material of the hose, as well as the outside temperature, just to name some of these factors.

Given this background, it is the object to provide a method and device for measuring and controlling the gas temperature, which overcomes the above disadvantages.

SUMMARY OF THE INVENTION

The method according to the invention is based, substantially, on that for measuring and controlling the gas temperature at the patient-side end of a heating device, a mathematical model is used. For this purpose, the complete system consisting of heating wire, electronic measurement system, supply line, temperature sensor, and gas flow is described by a set of differential equations and put together in a so-called state-space model. Under the condition that the parameters of the model are sufficiently precisely determined, then, with identical input variables, an estimation for the gas temperature at the exit of the gas hose, for example, can be made. By comparison of the actual and the estimated wire temperature, deviations (so-called observer errors) can be detected. They may occur, e.g., due to different initial states (e.g., there is no a priori information about the gas temperature at the beginning of the gas supply). If the observer error is rated with a performance criterion, and the result is then fed back to the model (state-variables correction), the error will go down, and as a result, a precise estimate for the gas temperature at the exit of the hose is obtained. The advantage of the proposed method is, among others, that for the measurement of the gas temperature at the exit of the hose, no additional temperature sensor is required. As a result, even without a temperature sensor at the exit of the hose, a precision of estimation is achieved that is comparable to the precision of measurement by means of a conventional hose including a temperature sensor. Safety for the patients is thus ensured even without an additional sensor.

Preferably, the method according to the invention is configured such that the estimation system is implemented as a state observer, in particular as a Luenberger observer. Such state observers including the Luenberger observer are described, e.g., in textbooks of control engineering.

A particular embodiment of such a device implementing the above method is an insufflation apparatus for laparoscopy. It comprises a gas supply (e.g., from a pressure bottle) that is provided with the required exit pressure, and is enabled to achieve a suitable volume flow. The volume flow is controllable, e.g., between 0 and 50l/min. Through a supply hose, the gas is introduced into the inward parts of the body. For obtaining the desired temperature (approx. body temperature, i.e., approx. 37° C.) at the exit of the hose, there is provided a heating device, e.g., a heating wire, in the interior of the hose. The gas introduced into the inward parts of the body may be discharged either through separate gas exit devices, through a suction apparatus or also simply through leaks from the inward parts of the body. By the above method according to the invention, using the measurement data from the heating wire (by means of resistance measurement, for example), the actual temperature at the exit of the hose is estimated and is controlled by variation of the heating power of the heating wire. Using a separate temperature sensor is not necessary: when using a heating wire the resistance of which is temperature-dependent, the measurement of the heating wire temperature can be made by a resistance measurement, so that no additional components are required.

An alternative embodiment of the invention comprises a respiratory apparatus. By the respiratory apparatus, oxygen or an oxygen-containing gas mixture is led into the lung of the patient. For respiration, wetting of the oxygen-containing gas mixture is absolutely necessary. For preventing condensation, as well as for obtaining a gas temperature that is acceptable for the patient, a resistance heating by an electrical heating wire is provided within the respiration hose. In an analogous manner as in the above device for laparoscopy, the heating wire can serve as a temperature sensor by using a corresponding resistance measurement. The actual temperature at the exit of the hose is estimated by the method according to the invention. By means of the estimated value, the heating power is electronically controlled. As a result, a device is obtained that ensures a precise measurement and control of the gas temperature at the entrance of the hose, even under most various respiration conditions.

BRIEF DESCRIPTIONS OF THE DRAWINGS

Embodiments of the invention are shown in the figures and are explained in more detail in the following:

FIG. 1 shows in a model representation a gas supply hose with an incorporated heating wire, wherein the reference numerals have the following meanings:
1.1 volume flow
1.2 $\vartheta_E$ gas entry temperature
1.3 observed heating wire control volume
1.4 $\xi$ ambient temperature
1.5 observed fluid control volume
1.6 $\eta$ hose temperature
1.7 $\sigma(R_{Dr})$ wire temperature
1.8 $\xi$ gas exit temperature
1.9 unheated length
1.10 heated length
1.11 observed hose control volume
1.12 exchanged amounts of heat
1.13 $U_{Dr}$ heating voltage FIG. 2 shows schematically the estimation process according to an embodiment of the invention;

FIG. 3 illustrates graphically a procedure for describing the behavior of the wire temperature over time;

FIG. 4 shows the resulting state-space model, which is dependent on the gas flow;

Figure 6:
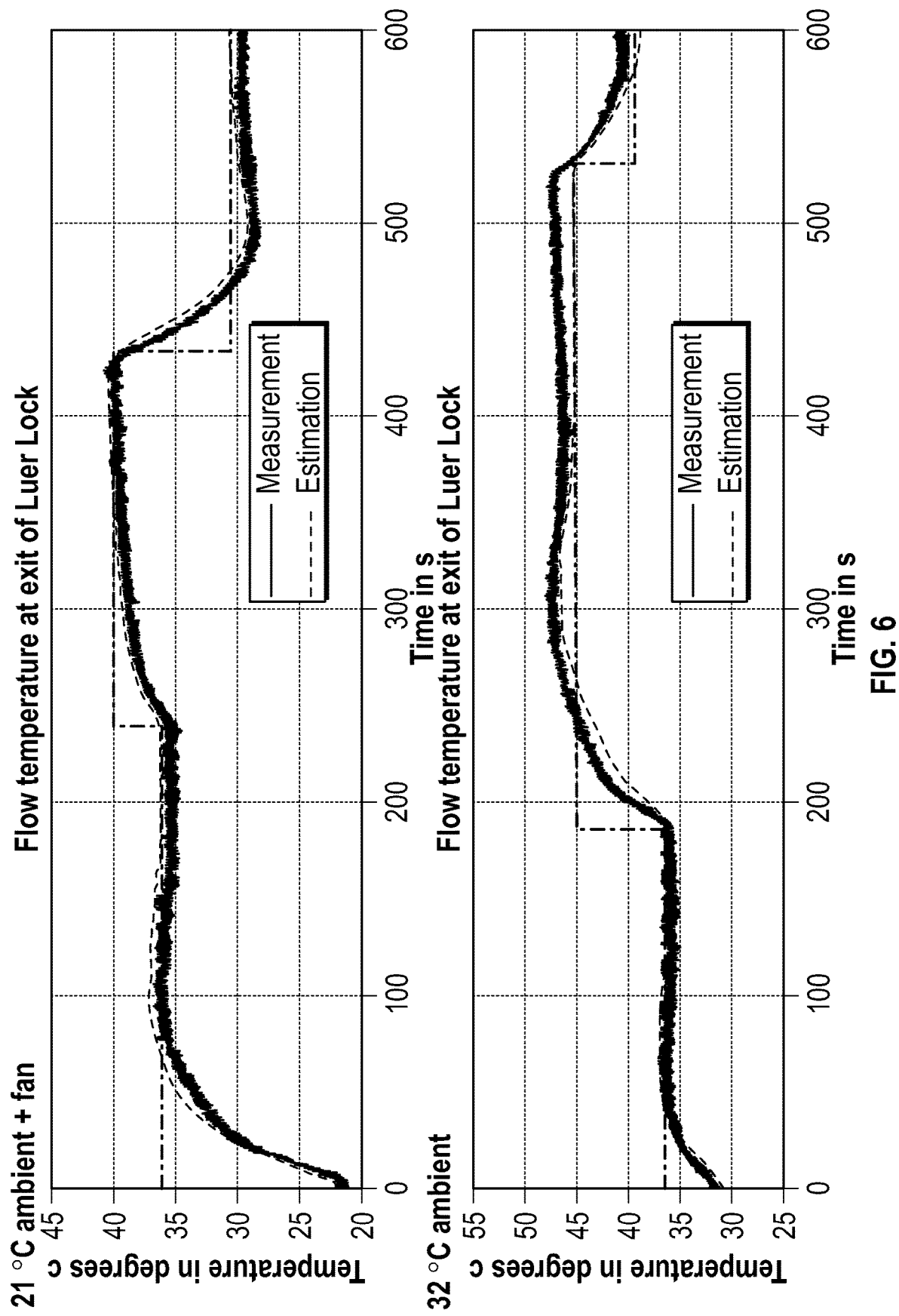
Figure 7A:
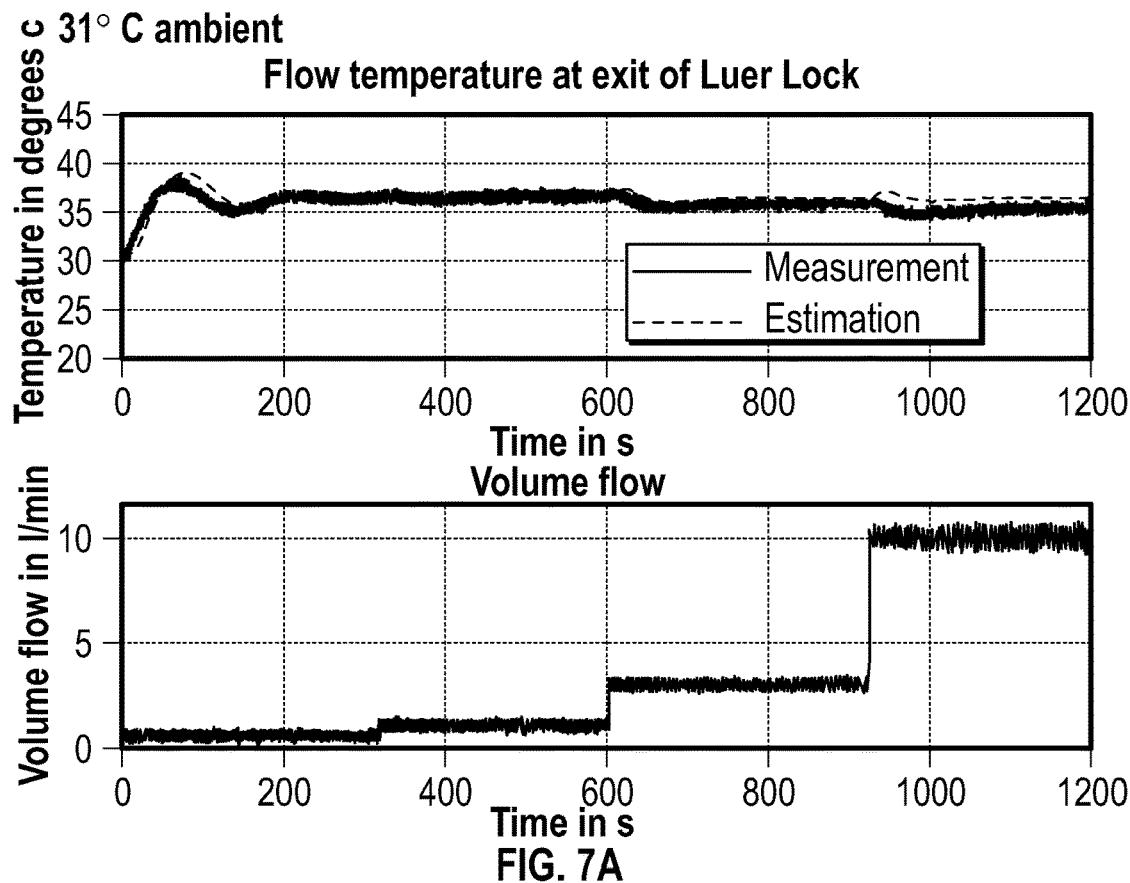
Figure 7B:
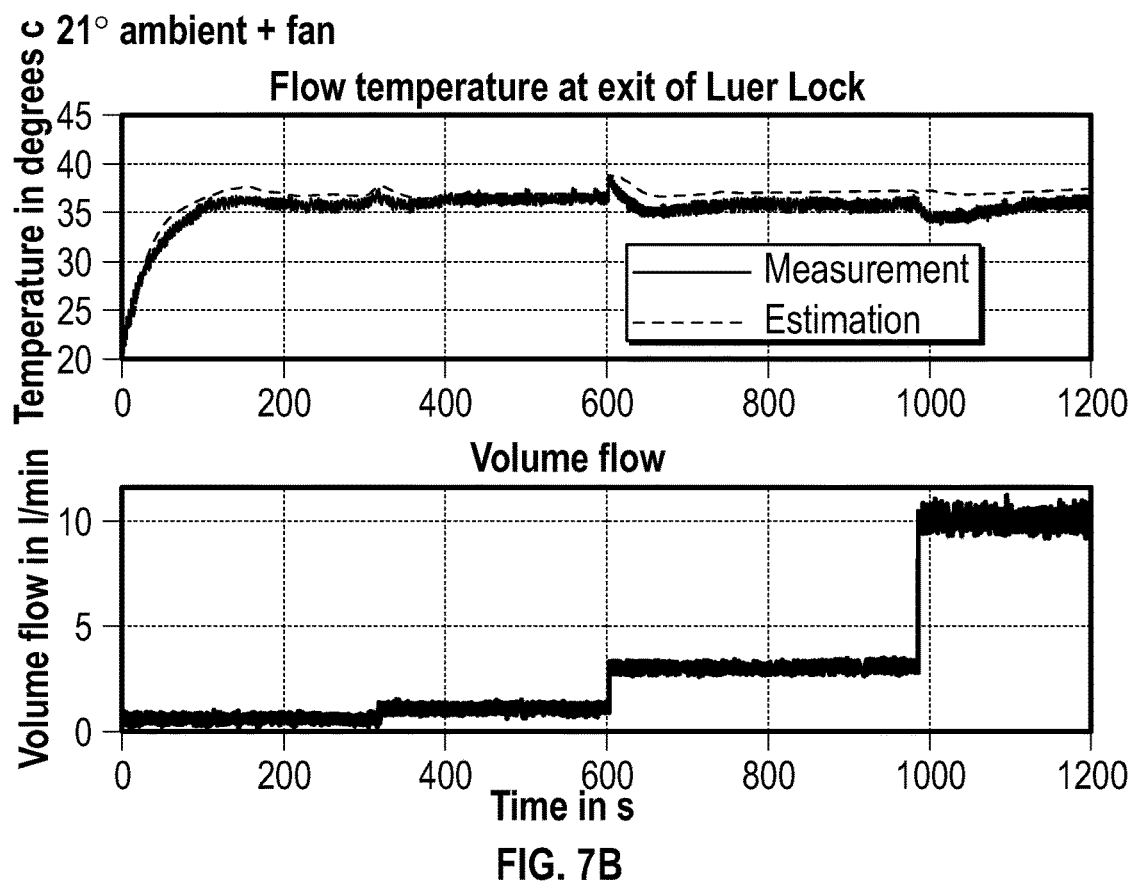
Figure 8:
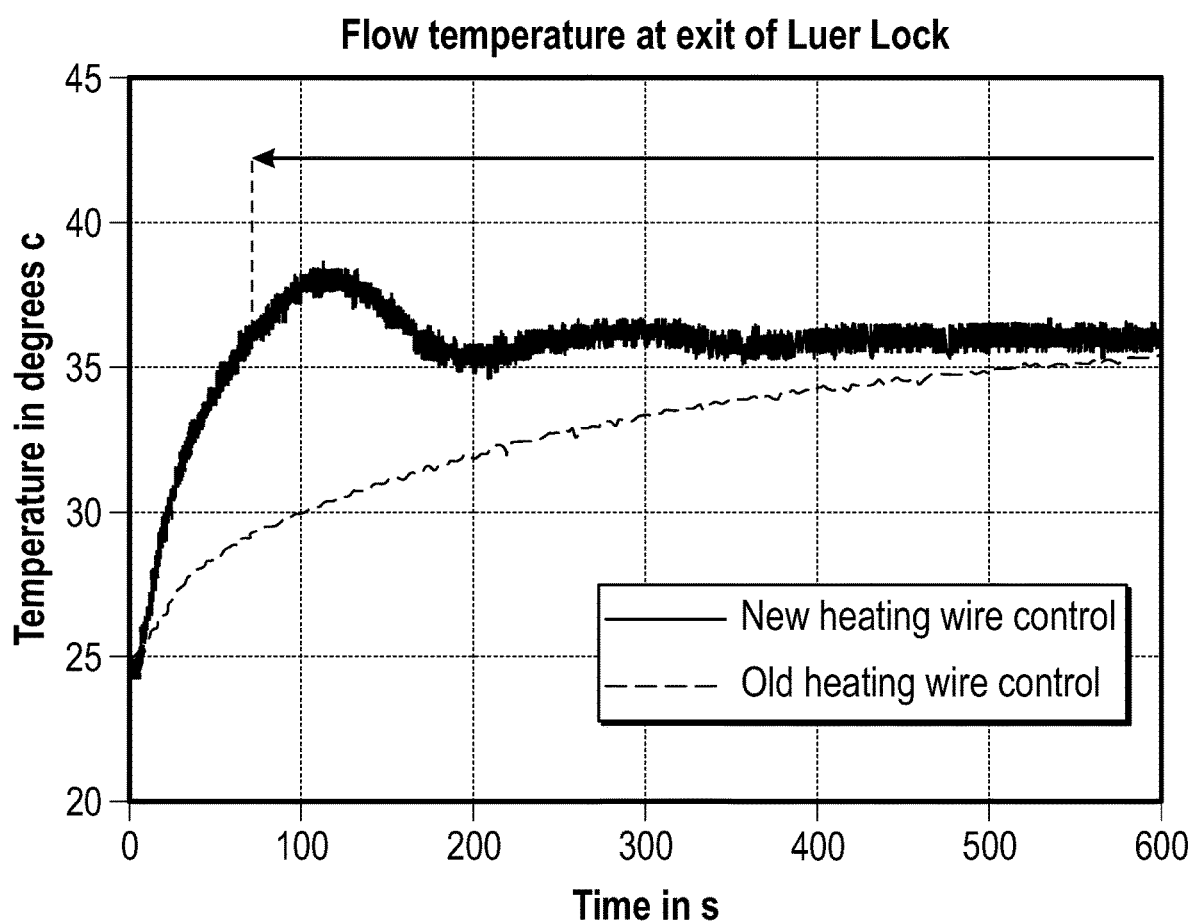
Figure 9:
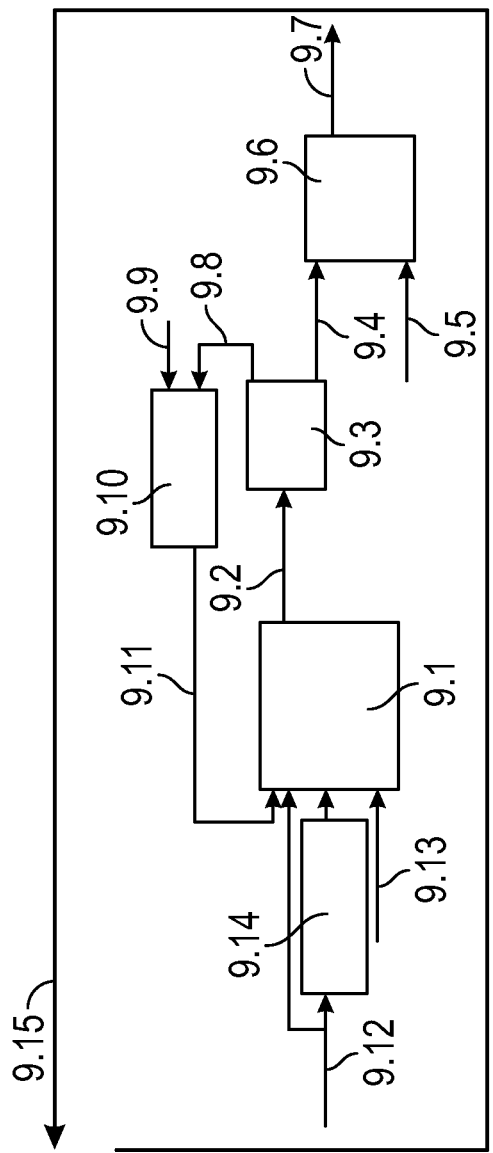

FIGS. 6, 7A and 7B show an embodiment of the method for different ambient conditions that were modeled as a disturbance; and FIG. 8 shows a comparison of the heating wire control according to an embodiment of the invention to a classic pre-control that only adjusts the power of the heating wire by the resistance of the heating wire; and FIG. 9 shows a sequence diagram of the software module according to an embodiment of the present disclosure.

DETAILED DESCRIPTION OF THE INVENTION

Reference will be made in detail to exemplary embodiments of the disclosure, which are illustrated in the accompanying figures and examples. Referring to the drawings in general, it will be understood that the illustrations are for the purpose of describing particular embodiments of the disclosure and are not intended to limit the same.

Referring now to the drawings, wherein like parts are marked throughout the specification and drawings with the same or similar reference numerals. Drawing figures are not necessarily to scale and in certain views, parts may have been exaggerated for purposes of clarity.

Figure 1:
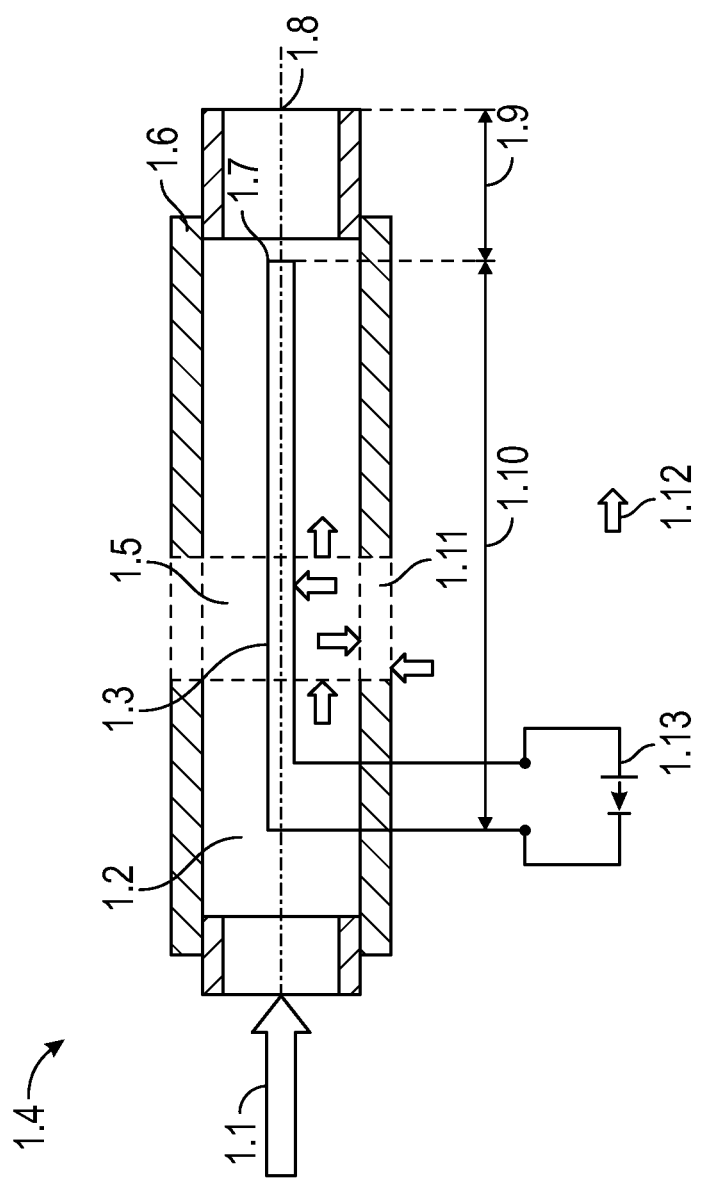

In the embodiment illustrated in FIG. 1, a gas volume flow flows through the hose in the direction of the arrow. However, corresponding to the length of the heating wire, in this model, only a partial length of the hose is heated. Then follow an unheated remaining length and a Luer adapter for the transition to the patient. The temperature of the heating wire is measured by resistance measurement. The temperature of the flow at the exit from the hose is to be measured for volume flows from 0 to 50 l/min in a range from 32° C. to 42° C.

Figure 2:
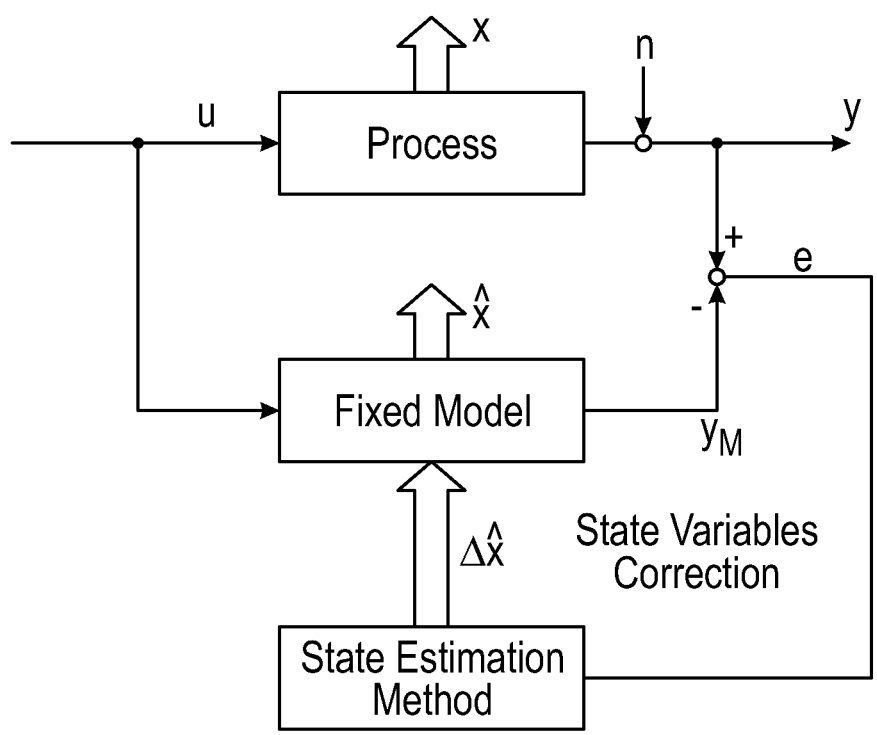

In this method, the volume flow, the temperature of the heating wire, the electrical power and the time courses thereof are continuously measured and processed. FIG. 2 (from Isermann R (2008). Mechatronische Systeme. Grundlagen. Springer-Verlag: Berlin) shows schematically the estimation process according to the an embodiment of the present invention. Control of the heating wire is performed, for instance, by a pulse-wide-modulated voltage (PWM). The electrical power (U in FIG. 2) and the wire resistance (Y in FIG. 2) are measured. The measurement data are subjected to a mathematical model ("fixed model" in FIG. 2), which illustrates the dynamic behavior of the system. For various flows, different model parameters are provided, so that the model can be adapted to the measured volume flow. The temperature value estimated by means of the model is compared to the measured actual value of the wire temperature (y-$y_M$ in FIG. 2). Deviations between the estimated value and the measured value (e in FIG. 2) are fed back to the model such that the estimation of the state variables is improved (state estimation method in FIG. 2). Once the estimate matches the actual value, the estimated state variables ($\hat{x}$ in FIG. 2) can be taken and further utilized. One of these state variables is the exit temperature of the gas flow, which consequently can precisely be estimated.

The method according to the invention presents a number of advantages. The observed temperature/state variable considers disturbances of the process (disturbance observer). The observed variable can be used as a control variable, so that the adjustment of different reference values is possible. Overall, a control performance will result that is comparable to the possible control performance when using a temperature sensor (for measurement of the flow temperature). A risk for the patient is thereby widely excluded, and the control process can be configured, by the omission of the flow temperature sensor, in a considerably more economic way. A particular advantage of the method according to the invention is that errors due to defective flow temperature sensors are excluded. Since in this method, sensor and actor are identical, there will fail, in case of a defect, both the measuring element and the actuator. Introducing heating power without a simultaneous verification by a temperature measurement is not possible.

For the estimation of the state variable (exit temperature), a mathematical model of the process is required. This mathematical model has a standardized form, called state-space model, which is represented in FIG. 4. For determining this state-space model, it is necessary to build-up a physical replacement model of the process and to bring it into this standardized form. The employed matrices have to be provided with values (identification). The procedure for describing the behavior of the wire temperature over time is shown exemplarily in FIG. 3, wherein the amount of heat exchanged between fluid and wire (equation 1), the amount of heat stored in the wire (equation 2), and the supplied amount of heat (equation 3) are described in the form of differential equations. Equation 4 then shows the energy balance (heat balance). By combining the equations and suitable operations thereon, equation 5 is obtained. Equation 6 shows as a comparison the applied state-space model, which is widely identical with equation 6, and coefficients of which contain the parameters of the model equations. A corresponding procedure is followed for modeling the gas and hose temperature (cf. FIG. 1).

FIG. 4 shows the resulting state-space model, which is dependent on the gas flow.

Figure 5:
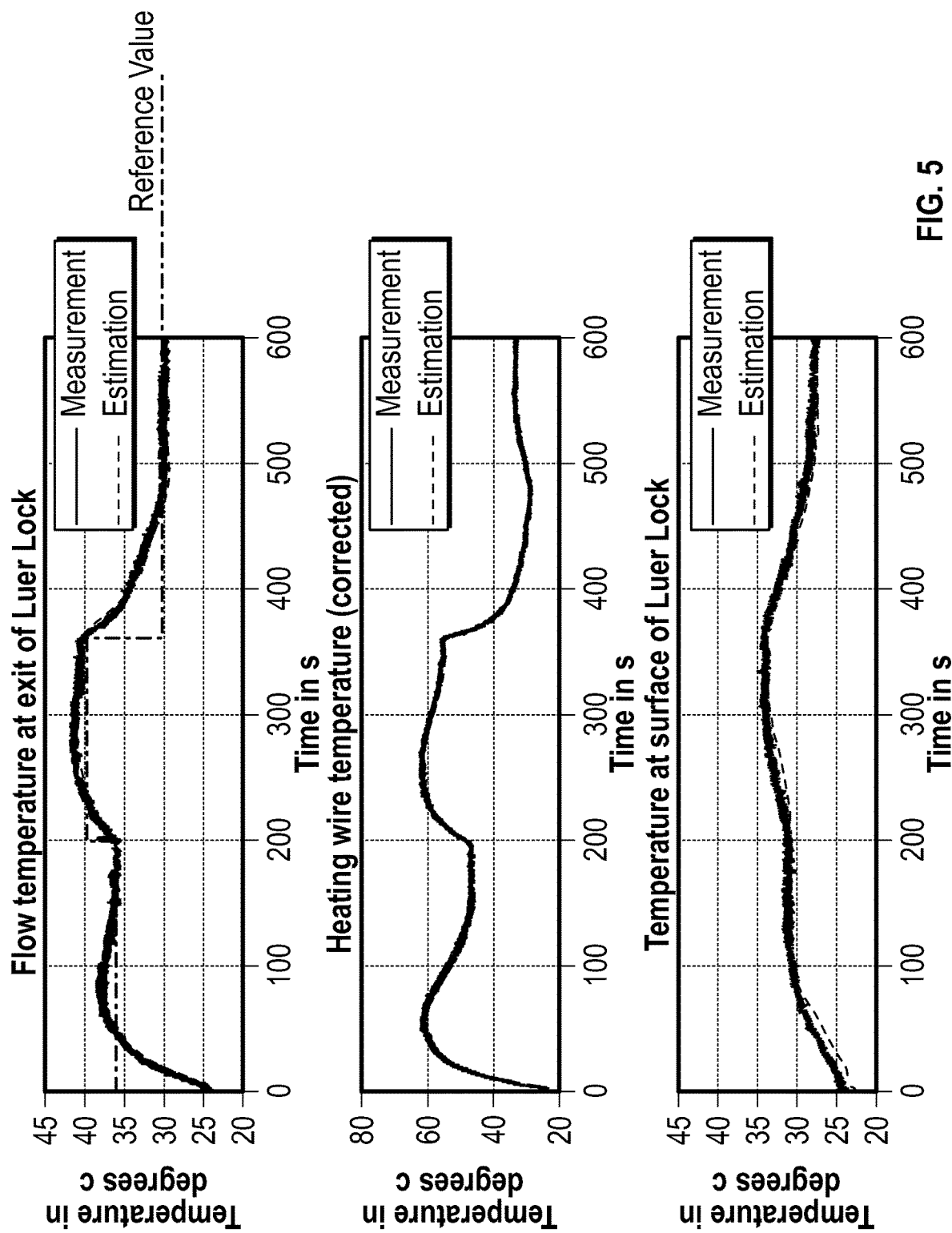
FIG. 5 shows the comparison of the actually measured data to the estimated data obtained by means of an embodiment of the method of the present disclosure.

FIG. 5 shows the comparison of the actually measured data to the estimated data obtained by means of the method. As a result, it is shown that the applied model is correct and leads to the necessary precision of the estimated data.

FIGS. 6 and 7 show the method for different ambient conditions that were modeled as a disturbance. The real application is subjected to a series of disturbances, such as, e.g., a different ambient temperature in FIG. 4) or a different gas entry temperature (SE in FIG. 4). The disturbances are provided in the state-space model. It can be seen a high agreement of the measured temperature with the estimated temperature, even with variation of the flow rate.

FIG. 8 shows a comparison of the heating wire control according to the invention to a classic pre-control that only adjusts the power of the heating wire by the resistance of the heating wire. As a result it can be seen that the method according to the invention can achieve the control very much faster.

The practical implementation of the above method is suitably achieved on a microcontroller that is part of the medical device. It is typically provided with inputs and out-puts and memories. The mathematical operations are performed in the form of a software module. A sequence diagram of the software module is shown in FIG. 9, wherein the reference numerals have the following meanings:

9.1 numerical solution of the observer differential equation
9.2 estimated state variables
9.3 separation of the state variables
9.4 estimated gas exit temperature
9.5 reference value for gas exit temperature
9.6 controller
9.7 heating wire voltage
9.8 estimated wire temperature
9.9 measured wire temperature
9.10 calculation observer error
9.11 observer error
9.12 measured volume flow
9.13 measured electrical power
9.14 calculation correction vector
9.15 numerical calculation: i=i+1

The software can be included on an own memory chip, e.g. an EPROM.

Those skilled in the art can, based on the present description including the figures and the technical literature known at the time of the application, implement further embodiments of the invention, without any further inventiveness being required.

What is claimed is:

1. A method for measuring and controlling the gas temperature in medical methods, comprising the steps of:
    supplying a gas to a patient using a gas supply device and a supply line, wherein the gas is supplied at a gas volume flow that is controllable between 0 and 50 l/min;
    heating the gas to a desired temperature using a heating system prior to the gas being provided to the patient, wherein heating occurs using a heating wire positioned within the supply line;
    electrically controlling the heating power of the heating wire based on an estimated value of a temperature of the gas at an exit of the heating system obtained from a mathematical estimation system that is configured as a state observer, wherein a resistance of the heating wire and current gas flow volume are used as input variables of the mathematical estimation system.

2. The method according to claim 1, wherein the state observer is configured as a Luenberger observer.

3. The method according to claim 1, wherein the gas is $CO_2$ or an oxygen-containing gas mixture.

4. The method according to claim 1, wherein the heating system is associated with the gas supply line and the gas is heated within the gas supply line.

5. The method according to claim 1, wherein the gas is supplied to the patient using an insufflator.

6. The method according to claim 1, wherein the gas is supplied to the patent using a respirator.

7. A medical device for supplying gases to patients comprising:
    a gas supply device that includes a gas supply line for supplying a gas to a patient, wherein the gas is supplied at a gas volume flow that is controllable, between 0 and 50 l/min ;
    a heating system which heats the gas to a desired temperature using a heating wire positioned within the supply line prior to the gas being provided; and
    a controller for electrically controlling the heating power of the heating wire based on an estimated value of an exit temperature of the gas at an exit of the heating system obtained from a mathematical estimation system that is configured as a state observer, wherein a resistance of the heating wire and current gas flow volume are used as is an-input variables of the mathematical estimation system.

8. The medical device according to claim 7, wherein the mathematical estimation system includes at least one microprocessor, at least one memory, and at least one software for determining the estimated value of the exit temperature.

9. The medical device according to claim 7, wherein the gas supply device is an insufflator for laparoscopy.

10. The medical device according to claim 7, wherein the gas supply device is a respiratory apparatus.

11. The medical device according to claim 7, wherein the gas is $CO_2$ or an oxygen-containing gas mixture.

12. The medical device according to claim 7, wherein the heating system is associated with the gas supply line and the gas is heated within the gas supply line.

13. The medical device according to claim 7, wherein the state observer is configured as a Luenberger observer.

* * * * *